United States Patent [19]
Sato et al.

[11] Patent Number: 6,037,521
[45] Date of Patent: Mar. 14, 2000

[54] TRANSGENIC MOUSE EXPRESSING AN β-AMYLOID TRANSGENE

[75] Inventors: Masahiro Sato, Kawagoe; Takashi Kobayashi, Fukuoka; Norihiro Tada, Kawagoe; Mikio Shoji, Gunma-gun; Takeshi Kawarabayashi, Maebashi, all of Japan

[73] Assignee: Hoechst Japan Limited, Tokyo, Japan

[21] Appl. No.: 08/339,708

[22] Filed: Nov. 14, 1994

[30] Foreign Application Priority Data

Nov. 12, 1993 [JP] Japan .................................. 5-306026

[51] Int. Cl.$^7$ .......................... A01K 67/00; A01K 67/027
[52] U.S. Cl. .................................. 800/18; 800/9; 800/12; 800/3; 424/9.1; 424/9.2
[58] Field of Search ............................. 800/2; 435/172.3; 424/9, 9.1, 9.2

[56] References Cited

U.S. PATENT DOCUMENTS

| 5,387,742 | 2/1995 | Cordell . |
| 5,672,805 | 9/1997 | Reve . |

FOREIGN PATENT DOCUMENTS

| 0 451 700 | 10/1991 | European Pat. Off. . |
| WO 89/06689 | 7/1989 | WIPO . |
| WO 91/19810 | 12/1991 | WIPO . |
| WO 92/06187 | 4/1992 | WIPO . |
| WO 92/13069 | 8/1992 | WIPO . |
| WO/93/02189 | 2/1993 | WIPO . |
| WO/93/14200 | 7/1993 | WIPO . |

OTHER PUBLICATIONS

Kawabata et al., "Amyloid Plaques, Neurofibrillary Tangles and Neuronal Loss in Brains of Transgenic Mice Overexpressing a C–Terminal Fragment of Human Amyloid Precursor Protein", Nature, vol. 356, No. 19, Mar. 1992, pp. 265, 476–478.

Wirak et al., "Deposits of Amyloid β Protein in the Central Nervous System of Transgenic Mice", Reports, Jul. 1991, pp. 323–325.

Quon et al., "Formation of β–amyloid Protein Deposits in Brains of Transgenic Mice", Nature, vol. 352, No. 18, Jul. 1991, pp. 239–241.

Kowall et al., "And in Vivo Model for the Neurodegenerative Effects of β Amyloid and Protection by Substance P", Proc. Natl. Acad. Sci. vol. 88, 1991, pp. 7247–7251.

Yankner et al., "Neurotoxicity of a Fragment of the Amyloid Precursor Associated with Alzheimer's Disease", Reports, 1989, pp. 417–419.

Esch et al., "Cleavage of Amyloid β Peptide During Constitutive Processing of its Precursor", Science, vol. 248, pp. 1122–1124.

Yoshioka et al., "The $^{717}$Val→Ile Substitution in Amyloid Precursor Protein is Associated with Familial Alzheimer's Disease Regardless of Ethnic Groups", Bichem. Biophys. Res. Commun., vol. 178, No. 3, Aug. 1991, pp. 1141–1146.

Naruse et al., "Mis–Sense Mutation Val→Ile in Exon 17 of Amyloid Precursor Protein Gene in Japanese Familial Alzheimer's Disease", Lancet, vol. 337, 1991, pp. 978–979.

Ponte et al., "A New A4 Amloid mRNA Contains a Domain Homologous to Serine Proteinase Inhibitors", Nature, vol. 331, No. 11, Feb. 1988, pp. 525–527.

Tanzi et al., "Protease Inhibitor Domain Encoded by an Amyloid Protein Precursor mRNA Associated with Alzheimer's Disease", Nature, vol. 331, No. 11, 1988, pp. 528–530.

Kitaguchi et al., "Novel Precursor of Alzheimer's Disease Amyloid Protein Shows Protease Inhibitory Activity", Nature, vol. 331, No. 11, 1988, pp. 530–532.

Kang et al., "The Precursor of Alzheimer's Disease Amyloid A4 Protein Resembles a Cell–surface Receptor", Nature, vol. 325, No. 19, 1987, pp. 733–735.

Golde et al., "Processing of the Amyloid Protein Precursor to Potentially Amyloidogenic Derivatives", Science, vol. 255, 1992, pp. 728–730.

Mullan et al., "A Pathogenic Mutation for Probable Alzheimer's Disease in the App Gene at the N–terminus of β–amyloid", Nature Genetics, vol. 1, 1992, pp. 345–347.

Murrell et al., "A Mutation in the Amyloid Precursor Protein Associated with Hereditary Alzheimer's Disease", Reports, 1991, vol. 254, pp. 97–99.

Goate et al., "Segregation of a Missense Mutation in the Amyloid Precursor Protein Gene with Familial Alzheimer's Disease", Nature, vol. 349, 1991, pp. 704–706.

Goldgaber et al., "Characterization and Chromosomal Localization if a cDNA Encoding Brain Amyloid of Alzheimer's Disease", Sci., vol. 235, 1987, pp. 877–887.

Shivers et al., "Alzheimer's Disease Amyloidogenic Glycoprotein: Expression Pattern in Rat Brain Suggests a Role in Cell Contact", EMBO Journ., vol. 7, No. 5, 1988, pp. 1365–1370.

Shoji et al., "The Amyloid β–Protein Precursor is Localized in Smooth Muscle Cells of Leptomeningeal Vessels", Brain Res., 530, 1990, pp. 113–116.

Shoji et al., "Rapid Communication: Alzheimer Amyloid β–Protein Precursor in Sperm Development", Amer. Journ. Path., vol. 137, No. 5, Nov. 1990, pp. 1027–1032.

(List continued on next page.)

*Primary Examiner*—Deborah Crouch
*Attorney, Agent, or Firm*—Foley & Lardner

[57] ABSTRACT

The invention relates to an animal model of human Alzheimer's disease that is useful for determining the mechanism of the disease and for developing and testing potential therapeutic drugs. More particularly, the present invention relates to the creation of transgenic non-human mammalian animals having integrated into their genome an exogenous DNA construct that encodes a portion of a β-amyloid precursor protein ("APP") and that is designed to overexpress in various types of animal tissues.

20 Claims, 9 Drawing Sheets

OTHER PUBLICATIONS

Shoji et al., "Amyloid β–Protein Precursor Accumulates in Dystrophic Neurites of Senile Plaques in Alzheimer–Type Dementia", Brain Res., 512, 1990, pp. 164–168.

Wong et al., "Neuritic Plaques and Cerebrovascular Amyloid in Alzheimer Disease are Antigenically Related", Proc. Natl. Acad. Sci., vol. 82, 1985, pp. 8729–8732.

Jon. W. Gordon, "Transgenic Animals", Inter. Rev. Cytology, vol. 115, pp. 171–229.

Palmiter et al., "Germ–Line Transformation of Mice", Ann. Rev. Genet., 1986, pp. 465–499.

Niwa et al., "Efficient Selection for High–Expression Transfectants with a Novel Eukaryotic Vector", Gene, vol. 108, 1991, pp. 193–200.

Nishimoto et al., "Alzheimer Amyloid Protein Precursor Complexes with Brain GTP–Binding Protein $G_o$", Nature, vol. 362, 1993, pp. 75–79.

Hardy et al., "Molecular Classification of Alzheimer's Disease", Lancet, col. 337, 1991, pp. 1342–1343.

"Alzheimer's Assasult", Sciencescope, Feb. 1992, p. 1059.

Chartier–Harlin et al., "Early–onset Alzheimer's Disease Caused by Mutations at Codon 717 of the β–amyloid Precursor Protein Gene", Nature, vol. 353, 1991, pp. 844–846.

Sandhu et al (1991) J. Biol. Chem. 266, 21331–21334.

Yamada et al (1989) Biochem. Biophys. Res. Comm. 153, 906–92.

van der Putten (1985) Proced. Natl. Acad. Sci. 82, 6148–6152.

Lemaire et al (1989) Nuc. Acids Res. 17, 517–523.

Schmidt et al (1990) Mol. Cell. Bio. 10, 4406–4411.

Levy et al (1990) Science 248, 1124–1126.

FUKUCHI, Ken–ichiro et al., "High Levels of Circulating β–Amyloid Peptide Do Not Cause Cerebral β–Amyloidosis in Transgenic Mice," American Journal of Pathology, Vol. 149, No. 1, Jul. 1996.

FUKUCHI, Ken–Ichiro et al., "Overexpression of a C–Terminal Portion of the β–Amyloid Precursor Protein in Mouse Brains by Transplantation of Transformed Neuronal Cells," Experimental Neurology, 127, 253–264 (1994).

FUKUCHI, Ken–ichiro et al., "Overexpression of Amyloid Precursor Protein Alters its Normal Processing and is Associated with Neurotoxicity," Biochemical and Biophysical Research Communications, Vol. 182, pp. 165–173 (1992).

CAI, Xiao–Dan et al., "Release of Excess Amyloid β Protein from a Mutant Amyloid β Protein Precursor," Science, Vol. 259, Jan. 22, 1993.

En : Cytomegalovirus enhancer

βA : Chicken β - actin promotor

▨ : APP coding region

SP : Signal peptide

β/A4 : C - terminal region of APP corresponding to β/A4 protein

* : Glu→Gln conversion at codon No. 22 in β/A4 protein

✦ : Val→Ile conversion at codon No. 50 in β/A4 protein

•• : Lys→Asn conversion at codon No. 3 and Met→Leu conversion at codon No. 4 in β/A4 protein

|   |   |    | |
|---|---|----|---|
| 1, | 6, | 11 | Brain |
| 2, | 7, | 12 | Liver |
| 3, | 8, | 12 | Kidney |
| 4, | 9, | 13 | Intestine |
| 5, | 10,| 15 | Testis |

| | | |
|---|---|---|
| 1 | Transgenic animal | ( 0202 ) |
| 2 | Transgenic animal | ( 0305 ) |
| 3 | Transgenic animal | ( 0401 ) |
| 4 | Transgenic animal | ( 0804 ) |
| 5 | Transgenic animal | ( 1002 ) |
| 6 | Transgenic animal | ( 1004 ) |
| 7 | Transgenic animal | ( 1301 ) |
| 8 | Transgenic animal | ( 1303 ) |
| 9 | Transgenic animal | ( 1402 ) |
| 10 | Transgenic animal | ( 1501 ) |
| 11 | Transgenic animal | ( 1804 ) |
| 12 | Non - transgenic animal | |

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
       (A) LENGTH: 51 base pairs
       (B) TYPE: nucleic acid
       (C) STRANDEDNESS: single
       (D) TOPOLOGY: linear (ii) MOLECULE TYPE: cDNA to mRNA (iii) HYPOTHETICAL: NO (iii) ANTI-SENSE: NO (vi) ORIGINAL SOURCE:
       (A) ORGANISM: homo sapiense
       (B) STRAIN: human brain (ix) FEATURE:
       (A) NAME/KEY: CDS
       (B) LOCATION: 1..51
       (D) OTHER INFORMATION: /note= "1. human beta-amyloid
          precursor; 2. signal peptide"

(xi) SEQUENCE DESCRIPTION: SEQ ID NO: 1:

```
ATG CTG CCC GGT TTG GCA CTG CTC CTG CTG GCC GCC TGG ACG GCT CGG      48
Met Leu Pro Gly Leu Ala Leu Leu Leu Leu Ala Ala Trp Thr Ala Arg
 1               5                  10                  15

GCG                                                                  51
Ala
```

(2) INFORMATION FOR SEQ ID NO: 2:

(i) SEQUENCE CHARACTERISTICS:
       (A) LENGTH: 17 amino acids
       (B) TYPE: amino acid
       (D) TOPOLOGY: linear (ii) MOLECULE TYPE: protein (xi) SEQUENCE DESCRIPTION: SEQ ID NO: 2:

```
Met Leu Pro Gly Leu Ala Leu Leu Leu Ala Ala Trp Thr Ala Arg
 1               5                  10                  15

Ala
```

(2) INFORMATION FOR SEQ ID NO: 3:

(i) SEQUENCE CHARACTERISTICS:
       (A) LENGTH: 297 base pairs
       (B) TYPE: nucleic acid
       (C) STRANDEDNESS: single
       (D) TOPOLOGY: linear (ii) MOLECULE TYPE: cDNA to mRNA (iii) HYPOTHETICAL: NO (iii) ANTI-SENSE: NO (vi) ORIGINAL SOURCE:
       (A) ORGANISM: homo sapiense
       (B) STRAIN: human brain (ix) FEATURE:
       (A) NAME/KEY: CDS (B) LOCATION: 1..297
           (D) OTHER INFORMATION: /note= "1. human beta-amyloid
               precursor; 2. C-terminal peptide"

(xi) SEQUENCE DESCRIPTION: SEQ ID NO: 3:

GAT GCA GAA TTC CGA CAT GAC TCA GGA TAT GAA GTT CAT CAT CAA AAA        48
Asp Ala Glu Phe Arg His Asp Ser Gly Tyr Glu Val His His Gln Lys
 1               5                  10                  15

TTG GTG TTC TTT GCA GAA GAT GTG GGT TCA AAC AAA GGT GCA ATC ATT        96
Leu Val Phe Phe Ala Glu Asp Val Gly Ser Asn Lys Gly Ala Ile Ile
                20                  25                  30

GGA CTC ATG GTG GGC GGT GTT GTC ATA GCG ACA GTG ATC GTC ATC ACC       144
Gly Leu Met Val Gly Gly Val Val Ile Ala Thr Val Ile Val Ile Thr
            35                  40                  45

TTG GTG ATG CTG AAG AAG AAA CAG TAC ACA TCC ATT CAT CAT GGT GTG       192
Leu Val Met Leu Lys Lys Lys Gln Tyr Thr Ser Ile His His Gly Val
        50                  55                  60

GTG GAG GTT GAC GCC GCT GTC ACC CCA GAG GAG CGC CAC CTG TCC AAG       240
Val Glu Val Asp Ala Ala Val Thr Pro Glu Glu Arg His Leu Ser Lys
 65                 70                  75                  80

ATG CAG CAG AAC GGC TAC GAA AAT CCA ACC TAC AAG TTC TTT GAG CAG       288
Met Gln Gln Asn Gly Tyr Glu Asn Pro Thr Tyr Lys Phe Phe Glu Gln
                85                  90                  95

ATG CAG AAC                                                            297
Met Gln Asn (2) INFORMATION FOR SEQ ID NO: 4:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 4:

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr Val Ile Val Ile Thr
            35                  40                  45

Leu Val Met Leu Lys Lys Lys Gln Tyr Thr Ser Ile His His Gly Val
        50                  55                  60

Val Glu Val Asp Ala Ala Val Thr Pro Glu Glu Arg His Leu Ser Lys
 65                 70                  75                  80

Met Gln Gln Asn Gly Tyr Glu Asn Pro Thr Tyr Lys Phe Phe Glu Gln
                85                  90                  95

Met Gln Asn (2) INFORMATION FOR SEQ ID NO: 5:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (vi) ORIGINAL SOURCE:
    (A) ORGANISM: homo sapiense
    (B) STRAIN: human brain (ix) FEATURE:
    (A) NAME/KEY: CDS
    (B) LOCATION: 1..297
    (D) OTHER INFORMATION: /note= "1. human beta-amyloid
        precursor; 2. C-terminal peptide"

(xi) SEQUENCE DESCRIPTION: SEQ ID NO: 5:

| GAT | GCA | GAA | TTC | CGA | CAT | GAC | TCA | GGA | TAT | GAA | GTT | CAT | CAT | CAA | AAA | 48 |
| Asp | Ala | Glu | Phe | Arg | His | Asp | Ser | Gly | Tyr | Glu | Val | His | His | Gln | Lys | |
| 1 | | | | 5 | | | | | 10 | | | | | 15 | | |

| TTG | GTG | TTC | TTT | GCA | CAA | GAT | GTG | GGT | TCA | AAC | AAA | GGT | GCA | ATC | ATT | 96 |
| Leu | Val | Phe | Phe | Ala | Gln | Asp | Val | Gly | Ser | Asn | Lys | Gly | Ala | Ile | Ile | |
| | | | | 20 | | | | | 25 | | | | | 30 | | |

| GGA | CTC | ATG | GTG | GGC | GGT | GTT | GTC | ATA | GCG | ACA | GTG | ATC | GTC | ATC | ACC | 144 |
| Gly | Leu | Met | Val | Gly | Gly | Val | Val | Ile | Ala | Thr | Val | Ile | Val | Ile | Thr | |
| | | 35 | | | | | 40 | | | | | 45 | | | | |

| TTG | GTG | ATG | CTG | AAG | AAG | AAA | CAG | TAC | ACA | TCC | ATT | CAT | CAT | GGT | GTG | 192 |
| Leu | Val | Met | Leu | Lys | Lys | Lys | Gln | Tyr | Thr | Ser | Ile | His | His | Gly | Val | |
| | 50 | | | | | 55 | | | | | 60 | | | | | |

| GTG | GAG | GTT | GAC | GCC | GCT | GTC | ACC | CCA | GAG | GAG | CGC | CAC | CTG | TCC | AAG | 240 |
| Val | Glu | Val | Asp | Ala | Ala | Val | Thr | Pro | Glu | Glu | Arg | His | Leu | Ser | Lys | |
| 65 | | | | 70 | | | | | 75 | | | | | 80 | | |

| ATG | CAG | CAG | AAC | GGC | TAC | GAA | AAT | CCA | ACC | TAC | AAG | TTC | TTT | GAG | CAG | 288 |
| Met | Gln | Gln | Asn | Gly | Tyr | Glu | Asn | Pro | Thr | Tyr | Lys | Phe | Phe | Glu | Gln | |
| | | | | 85 | | | | | 90 | | | | | 95 | | |

| ATG | CAG | AAC | | | | | | | | | | | | | | 297 |
| Met | Gln | Asn | | | | | | | | | | | | | | |

(2) INFORMATION FOR SEQ ID NO: 6:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 6:

| Asp | Ala | Glu | Phe | Arg | His | Asp | Ser | Gly | Tyr | Glu | Val | His | His | Gln | Lys |
| 1 | | | | 5 | | | | | 10 | | | | | 15 | |

| Leu | Val | Phe | Phe | Ala | Gln | Asp | Val | Gly | Ser | Asn | Lys | Gly | Ala | Ile | Ile |
| | | | | 20 | | | | | 25 | | | | | 30 | |

| Gly | Leu | Met | Val | Gly | Gly | Val | Val | Ile | Ala | Thr | Val | Ile | Val | Ile | Thr |
| | | 35 | | | | | 40 | | | | | 45 | | | |

| Leu | Val | Met | Leu | Lys | Lys | Lys | Gln | Tyr | Thr | Ser | Ile | His | His | Gly | Val |
| | 50 | | | | | 55 | | | | | 60 | | | | |

| Val | Glu | Val | Asp | Ala | Ala | Val | Thr | Pro | Glu | Glu | Arg | His | Leu | Ser | Lys |
| 65 | | | | 70 | | | | | 75 | | | | | 80 | |

| Met | Gln | Gln | Asn | Gly | Tyr | Glu | Asn | Pro | Thr | Tyr | Lys | Phe | Phe | Glu | Gln |
| | | | | 85 | | | | | 90 | | | | | 95 | |

Met Gln Asn (2) INFORMATION FOR SEQ ID NO: 7:

(i) SEQUENCE CHARACTERISTICS:
        (A) LENGTH: 297 base pairs
        (B) TYPE: nucleic acid
        (C) STRANDEDNESS: single (D) TOPOLOGY: linear (ii) MOLECULE TYPE: cDNA to mRNA (iii) HYPOTHETICAL: NO (iii) ANTI-SENSE: NO (vi) ORIGINAL SOURCE:
                    (A) ORGANISM: homo sapiense
                    (B) STRAIN: human brain (ix) FEATURE:
                    (A) NAME/KEY: CDS
                    (B) LOCATION: 1..297
                    (D) OTHER INFORMATION: /note= "1. human beta-amyloid
                        precursor; 2. C-terminal peptide"

(xi) SEQUENCE DESCRIPTION: SEQ ID NO: 7:

```
GAT GCA GAA TTC CGA CAT GAC TCA GGA TAT GAA GTT CAT CAT CAA AAA        48
Asp Ala Glu Phe Arg His Asp Ser Gly Tyr Glu Val His His Gln Lys
 1               5                  10                  15

TTG GTG TTC TTT GCA GAA GAT GTG GGT TCA AAC AAA GGT GCA ATC ATT        96
Leu Val Phe Phe Ala Glu Asp Val Gly Ser Asn Lys Gly Ala Ile Ile
                20                  25                  30

GGA CTC ATG GTG GGC GGT GTT GTC ATA GCG ACA GTG ATC ATC ATC ACC       144
Gly Leu Met Val Gly Gly Val Val Ile Ala Thr Val Ile Ile Ile Thr
         35                  40                  45

TTG GTG ATG CTG AAG AAG AAA CAG TAC ACA TCC ATT CAT CAT GGT GTG       192
Leu Val Met Leu Lys Lys Lys Gln Tyr Thr Ser Ile His His Gly Val
     50                  55                  60

GTG GAG GTT GAC GCC GCT GTC ACC CCA GAG GAG CGC CAC CTG TCC AAG       240
Val Glu Val Asp Ala Ala Val Thr Pro Glu Glu Arg His Leu Ser Lys
 65                  70                  75                  80

ATG CAG CAG AAC GGC TAC GAA AAT CCA ACC TAC AAG TTC TTT GAG CAG       288
Met Gln Gln Asn Gly Tyr Glu Asn Pro Thr Tyr Lys Phe Phe Glu Gln
                 85                  90                  95

ATG CAG AAC                                                           297
Met Gln Asn
```

(2) INFORMATION FOR SEQ ID NO: 8:

(i) SEQUENCE CHARACTERISTICS:
                (A) LENGTH: 99 amino acids
                (B) TYPE: amino acid
                (D) TOPOLOGY: linear (ii) MOLECULE TYPE: protein (xi) SEQUENCE DESCRIPTION: SEQ ID NO: 8:

```
Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr Val Ile Ile Ile Thr
         35                  40                  45

Leu Val Met Leu Lys Lys Lys Gln Tyr Thr Ser Ile His His Gly Val
     50                  55                  60

Val Glu Val Asp Ala Ala Val Thr Pro Glu Glu Arg His Leu Ser Lys
 65                  70                  75                  80

Met Gln Gln Asn Gly Tyr Glu Asn Pro Thr Tyr Lys Phe Phe Glu Gln
                 85                  90                  95

Met Gln Asn
```

(2) INFORMATION FOR SEQ ID NO: 9:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (vi) ORIGINAL SOURCE:
        (A) ORGANISM: homo sapiense
        (B) STRAIN: human brain (ix) FEATURE:
        (A) NAME/KEY: CDS
        (B) LOCATION: 1..309
        (D) OTHER INFORMATION: /note= "1. human beta-amyloid
            precursor; 2. C-terminal peptide"

(xi) SEQUENCE DESCRIPTION: SEQ ID NO: 9:

```
GAA GTG AAG ATG GAT GCA GAA TTC CGA CAT GAC TCA GGA TAT GAA GTT        48
Glu Val Lys Met Asp Ala Glu Phe Arg His Asp Ser Gly Tyr Glu Val
 1               5                  10                  15

CAT CAT CAA AAA TTG GTG TTC TTT GCA GAA GAT GTG GGT TCA AAC AAA        96
His His Gln Lys Leu Val Phe Phe Ala Glu Asp Val Gly Ser Asn Lys
                20                  25                  30

GGT GCA ATC ATT GGA CTC ATG GTG GGC GGT GTT GTC ATA GCG ACA GTG       144
Gly Ala Ile Ile Gly Leu Met Val Gly Gly Val Val Ile Ala Thr Val
            35                  40                  45

ATC GTC ATC ACC TTG GTG ATG CTG AAG AAG AAA CAG TAC ACA TCC ATT       192
Ile Val Ile Thr Leu Val Met Leu Lys Lys Lys Gln Tyr Thr Ser Ile
        50                  55                  60

CAT CAT GGT GTG GTG GAG GTT GAC GCC GCT GTC ACC CCA GAG GAG CGC       240
His His Gly Val Val Glu Val Asp Ala Ala Val Thr Pro Glu Glu Arg
65                  70                  75                  80

CAC CTG TCC AAG ATG CAG CAG AAC GGC TAC GAA AAT CCA ACC TAC AAG       288
His Leu Ser Lys Met Gln Gln Asn Gly Tyr Glu Asn Pro Thr Tyr Lys
                85                  90                  95

TTC TTT GAG CAG ATG CAG AAC                                           309
Phe Phe Glu Gln Met Gln Asn
               100
```

(2) INFORMATION FOR SEQ ID NO: 10:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO: 10:

```
Glu Val Lys Met Asp Ala Glu Phe Arg His Asp Ser Gly Tyr Glu Val
 1               5                  10                  15

His His Gln Lys Leu Val Phe Phe Ala Glu Asp Val Gly Ser Asn Lys
                20                  25                  30

Gly Ala Ile Ile Gly Leu Met Val Gly Gly Val Val Ile Ala Thr Val
            35                  40                  45

Ile Val Ile Thr Leu Val Met Leu Lys Lys Lys Gln Tyr Thr Ser Ile
        50                  55                  60
```

```
His His Gly Val Val Glu Val Asp Ala Ala Val Thr Pro Glu Glu Arg
 65                  70                  75                  80

His Leu Ser Lys Met Gln Gln Asn Gly Tyr Glu Asn Pro Thr Tyr Lys
             85                  90                  95

Phe Phe Glu Gln Met Gln Asn
            100
```

(2) INFORMATION FOR SEQ ID NO: 11:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (vi) ORIGINAL SOURCE:
        (A) ORGANISM: homo sapiense
        (B) STRAIN: human brain (ix) FEATURE:
        (A) NAME/KEY: CDS
        (B) LOCATION: 1..309
        (D) OTHER INFORMATION: /note= "1. human beta-amyloid
            precursor; 2. C-terminal peptide"

(xi) SEQUENCE DESCRIPTION: SEQ ID NO: 11:

```
GAA GTG AAT CTG GAT GCA GAA TTC CGA CAT GAC TCA GGA TAT GAA GTT      48
Glu Val Asn Leu Asp Ala Glu Phe Arg His Asp Ser Gly Tyr Glu Val
 1               5                  10                  15

CAT CAT CAA AAA TTG GTG TTC TTT GCA GAA GAT GTG GGT TCA AAC AAA      96
His His Gln Lys Leu Val Phe Phe Ala Glu Asp Val Gly Ser Asn Lys
             20                  25                  30

GGT GCA ATC ATT GGA CTC ATG GTG GGC GGT GTT GTC ATA GCG ACA GTG     144
Gly Ala Ile Ile Gly Leu Met Val Gly Gly Val Val Ile Ala Thr Val
         35                  40                  45

ATC GTC ATC ACC TTG GTG ATG CTG AAG AAG AAA CAG TAC ACA TCC ATT     192
Ile Val Ile Thr Leu Val Met Leu Lys Lys Lys Gln Tyr Thr Ser Ile
 50                  55                  60

CAT CAT GGT GTG GTG GAG GTT GAC GCC GCT GTC ACC CCA GAG GAG CGC     240
His His Gly Val Val Glu Val Asp Ala Ala Val Thr Pro Glu Glu Arg
 65                  70                  75                  80

CAC CTG TCC AAG ATG CAG CAG AAC GGC TAC GAA AAT CCA ACC TAC AAG     288
His Leu Ser Lys Met Gln Gln Asn Gly Tyr Glu Asn Pro Thr Tyr Lys
             85                  90                  95

TTC TTT GAG CAG ATG CAG AAC                                          309
Phe Phe Glu Gln Met Gln Asn
            100
```

(2) INFORMATION FOR SEQ ID NO: 12:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO: 12:

```
Glu Val Asn Leu Asp Ala Glu Phe Arg His Asp Ser Gly Tyr Glu Val
 1               5                  10                  15
```

```
His His Gln Lys Leu Val Phe Phe Ala Glu Asp Val Gly Ser Asn Lys
             20                   25                  30

Gly Ala Ile Ile Gly Leu Met Val Gly Gly Val Val Ile Ala Thr Val
             35                   40                  45

Ile Val Ile Thr Leu Val Met Leu Lys Lys Lys Gln Tyr Thr Ser Ile
 50                       55                  60

His His Gly Val Val Glu Val Asp Ala Ala Val Thr Pro Glu Glu Arg
 65                  70                  75                  80

His Leu Ser Lys Met Gln Gln Asn Gly Tyr Glu Asn Pro Thr Tyr Lys
             85                   90                  95

Phe Phe Glu Gln Met Gln Asn
            100
```

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: YES (vi) ORIGINAL SOURCE:
        (A) ORGANISM: none
        (B) STRAIN: none (ix) FEATURE:
        (A) NAME/KEY: exon
        (B) LOCATION: 1..26
        (D) OTHER INFORMATION: /note= "reverse primer DNA, termed
            "BAPP-6""

(xi) SEQUENCE DESCRIPTION: SEQ ID NO: 13:

TTCTGCATCC GCCCGAGCCG TCCAGG                                        26

(2) INFORMATION FOR SEQ ID NO: 14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: NO (vi) ORIGINAL SOURCE:
        (A) ORGANISM: none
        (B) STRAIN: none (ix) FEATURE:
        (A) NAME/KEY: exon
        (B) LOCATION: 1..29
        (D) OTHER INFORMATION: /note= "sense primer DNA, termed
            "BAPP-7""

(xi) SEQUENCE DESCRIPTION: SEQ ID NO: 14:

GCTCGGGCGG ATGCAGAATT CCGACATGA                                    29

(2) INFORMATION FOR SEQ ID NO: 15:

```
        (i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iii) ANTI-SENSE: NO (vi) ORIGINAL SOURCE:
            (A) ORGANISM: none
            (B) STRAIN: none (ix) FEATURE:
            (A) NAME/KEY: exon
            (B) LOCATION: 1..25
            (D) OTHER INFORMATION: /note= "sense primer DNA, termed
                "BAPP-10""

(xi) SEQUENCE DESCRIPTION: SEQ ID NO: 15:

CTCTAGAGAT GCTGCCCGGT TTGGC                                              25

(2) INFORMATION FOR SEQ ID NO: 16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iii) ANTI-SENSE: YES (vi) ORIGINAL SOURCE:
            (A) ORGANISM: none
            (B) STRAIN: none (ix) FEATURE:
            (A) NAME/KEY: exon
            (B) LOCATION: 1..30
            (D) OTHER INFORMATION: /note= "reverse primer DNA, termed
                "BAPP-12""

(xi) SEQUENCE DESCRIPTION: SEQ ID NO: 16:

GGCTCTAGAG CATGTTCTGC ATCTGCTCAA                                         30

(2) INFORMATION FOR SEQ ID NO: 17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (iii) ANTI-SENSE: YES (vi) ORIGINAL SOURCE:
            (A) ORGANISM: none
            (B) STRAIN: none (ix) FEATURE:
            (A) NAME/KEY: exon
            (B) LOCATION: 1..21
            (D) OTHER INFORMATION: /note= "reverse primer DNA, termed
                "BAPP-8""
```

(xi) SEQUENCE DESCRIPTION: SEQ ID NO: 17:

GTCTTGTGCA AAGAACACCA A                                              21

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: NO (vi) ORIGINAL SOURCE:
        (A) ORGANISM: none
        (B) STRAIN: none (ix) FEATURE:
        (A) NAME/KEY: exon
        (B) LOCATION: 1..21
        (D) OTHER INFORMATION: /note= "sense primer DNA, termed
            "BAPP-2""

(xi) SEQUENCE DESCRIPTION: SEQ ID NO: 18:

TTGGTGTTCT TTGCACAAGA T                                              21

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: YES (vi) ORIGINAL SOURCE:
        (A) ORGANISM: none
        (B) STRAIN: none (ix) FEATURE:
        (A) NAME/KEY: exon
        (B) LOCATION: 1..24
        (D) OTHER INFORMATION: /note= "reverse primer DNA, termed
            "BAPP-15""

(xi) SEQUENCE DESCRIPTION: SEQ ID NO: 19:

GGATCCAACT TCAGAGGCTG CTGT                                           24

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: YES (vi) ORIGINAL SOURCE:

```
        (A) ORGANISM: none
        (B) STRAIN: none (ix) FEATURE:
        (A) NAME/KEY: exon
        (B) LOCATION: 1..21
        (D) OTHER INFORMATION: /note= "reverse primer DNA, termed
            "BAPP-3""

(xi) SEQUENCE DESCRIPTION: SEQ ID NO: 20:

GGTGATGATG ATCACTGTCG C                                              21

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: NO (vi) ORIGINAL SOURCE:
        (A) ORGANISM: none
        (B) STRAIN: none (ix) FEATURE:
        (A) NAME/KEY: exon
        (B) LOCATION: 1..21
        (D) OTHER INFORMATION: /note= "sense primer DNA, termed
            "BAPP-9""

(xi) SEQUENCE DESCRIPTION: SEQ ID NO: 21:

GCGACAGTGA TCATCATCAC C                                              21

(2) INFORMATION FOR SEQ ID NO: 22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: NO (vi) ORIGINAL SOURCE:
        (A) ORGANISM: none
        (B) STRAIN: none (ix) FEATURE:
        (A) NAME/KEY: exon
        (B) LOCATION: 1..38
        (D) OTHER INFORMATION: /note= "sense primer DNA, termed
            "BAPP-13""

(xi) SEQUENCE DESCRIPTION: SEQ ID NO: 22:

GGCTCTAGAG ATGGAAGTGA AGATGGATGC AGAATTCC                             38

(2) INFORMATION FOR SEQ ID NO: 23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear
```

-continued

```
    (ii) MOLECULE TYPE: DNA (genomic)

(iii) HYPOTHETICAL: YES (iii) ANTI-SENSE: NO (vi) ORIGINAL SOURCE:
         (A) ORGANISM: none
         (B) STRAIN: none (ix) FEATURE:
         (A) NAME/KEY: exon
         (B) LOCATION: 1..38
         (D) OTHER INFORMATION: /note= "sense primer DNA, termed
             "BAPP-14""

(xi) SEQUENCE DESCRIPTION: SEQ ID NO: 23:

GGCTCTAGAG ATGGAAGTGA ATCTGGATGC AGAATTCC                                38
```

TRANSGENIC MOUSE EXPRESSING AN β-AMYLOID TRANSGENE

BACKGROUND OF THE INVENTION

1. Field of the Invention

This invention relates in general to an animal model that is useful for developing therapeutic drugs of a disease. More specifically, the present invention relates to the creation of a transgenic animal having an exogenous gene construct coding a part of β-amyloid precursor protein (hereinafter called APP) in its genome. The exogenous gene construct is designed to overexpress in various types of the cells.

2. Description of the Prior Art

Recent development of genetic engineering has made it possible to create embryos (so-called transformed embryos) into which a gene construct is integrated by microinjection of an exogenous gene construct (DNA) into the nuclei of 1-cell stage embryos or by infection of preimplantation embryos with retroviral vector DNA (Gordon et al., Proc. Natl. Acad. Sci., U.S.A., 77: 7380 (1980); Jaenisch et al., Cell, 32: 209 (1983). The resulting embryos can further develop to full term after the transfer into the oviducts/uteri of recipient foster mothers. Some of the resulting adult animals have the exogenous DNA integrated into their genome and to express the DNA in its tissues. These "transformed" animals are generally called transgenic animals (Gordon et al., Science, 214: 1244 (1981). The integrated exogenous DNA is called a transgene, generally consisting of a promoter and a target gene (encoding a protein that is desired to be expressed) and other regulator sequences. Expression of the transgene can occur even before maturation; for example, in some cases, the expression occurs in the cleavage stage of an embryo. As a result of the expression, a protein encoded by the transgene is produced. If this protein plays a crucial role on the morphogenetic pathway of individuals, some phenotypic alteration may occur at a certain stage of development. To provide phenotypic alteration in transgenic animals, two approaches are possible; 1) overexpression of a target protein in a targeted tissue(s) and 2) suppression of endogenous target gene expression by anti-sense gene technology (see. e.g., Katsuki et al., Science, 241: 593 (1988)). These are based upon an usage of tissue-specific or ubiquitous promoter and/or enhancer, both of which should be placed upstream of the target gene.

There are many reports that demonstrate that transgenic animals exhibit alteration of their original phenotypes due to expression of a transgene. These are mentioned in detail in the reviews by Palmiter et al. Annu. Rev. of Genet. 20: 465 (1986) and Cordon, Int. Rev. of Cytobiol. 115: 171 (1989), among others. These transgenic animals can be utilized in the fields of 1) analysis of gene expression in vivo during embryogenesis, 2) gene therapy for overcoming hereditary genetical diseases, and, 3) as a test system for pharmaceutical compositions. Transformation of an embryo with DNA can be achieved by giving the DNA exogenously; the added DNA then will be integrated into a part of DNA sequence in the chromosomes of the host embryos. Several techniques are known for introducing the exogenous DNA into mammalian embryos. For example, DNA may be introduced via a micropipett (so-called microinjection method) into the pronuclei of one-cell stage embryos (Gordon et al., 1980, above).

By using microinjection method, mammalian embryos into which DNA is injected can develop to full term after transfer to the oviducts or uteri of pseudopregnant female recipients. The progeny can be analyzed later by PCR (polymerase chain reaction) and/or Southern blot method to determine whether or not they have the injected DNA in their chromosomes. If the presence of the exogenous DNA is confirmed, the transgenic animals can next analyzed for gene expression by Northern blot hybridization or immunohistochemical methods. In this way, it is possible to introduce a certain human hereditary disease-like character into an animal.

Alzheimer's disease (hereinafter called AD) is considered, as mentioned later in detail, to be caused by overexpression of APP (Terry et al., Ann Neurol, 14: 496 (1983)). In the brains of patients with AD, there are observed neurofibrillary tangles (hereinafter called NFT), paired helical filaments (hereinafter called PHF), a neuritic plaque (or a senile plaque) and deposition of cerebral amyloid which are peculiar to AD; the latter two structures are derived from APP. Moreover, mutations in the APP gene have been recently found in familial Alzheimer's disease (hereinafter called FAD) and in hereditary cerebral amyloid angiopathy. In addition, it has been reported that amyloid plaque core protein (hereinafter called APCP), one of major components of cerebral amyloid, or D-amyloid core protein (later renamed D-protein or D/A4 protein; hereinafter called fl/A4 protein) is toxic to neurons (Yankner et al., Science, 245: 417 (1989)). From these data, it is considered that the most essential approach to elucidate the pathogenesis of AD is to analyze how fl/A4 protein is metabolized from APP and finally deposited in a brain.

As mentioned previously, there are two distinct morphological and pathological changes associated with AD, namely, formation of PHF and deposition of cerebral amyloid. PHF appears more often in other neuronal diseases than AD; whereas, both the neuritic plaque which is an amyloid deposit generated in an intercellular space of neurons and amyloid deposited in the periphery of cerebral blood vessels are considered to be specific for AD. Interestingly, the neuritic plaques are also observed in the brain of aged patients with Down's syndrome (AD is also occurring). Amyloid proteins, a major component of the neuritic plaque, were partially purified and found to consist of mainly β/A4 protein with about 4.2 kD comprising 39 to 42 amino acids (Glenner et al., BBRC, 120: 1131 (1984)). The amino acid sequence of β/A4 protein was determined (Glenner et al., 1984; Masters et al., Proc. Natl. Acad. Sci. U.S.A., 82: 4245 (1985) and proved different from the proteins previously reported so far.

A cDNA encoding APP, a relatively large protein precursor including β/A4 protein part, was recently isolated from the cDNA library of human embryonic cerebral tissues. Analysis of the DNA sequence of human APP cDNA revealed that human APP consists of 695 amino acids (hereinafter called A695), and β/A4 protein corresponds to the amino acid positions at 597 to 695 (Kang at al, Nature, 325: 733 (1987)). Furthermore, beside A695, successful isolation of other two cDNAs for larger APPs (hereinafter called A751 and A770, respectively) was reported (Kitaguchi at al., Nature, 331: 530 (1988)). A751 is a protein consisting A695 with a 56-amino acid insert. The 56-amino acid insert shows a high homology to serine protease inhibitor (hereinafter called KPI) of Kunitz family (Kitaguchi et al., 1988). A770 is a protein in which a 19 amino acid sequence highly homologous to MRC OX-2 antigen is inserted immediately after the 56 amino acid insert in A751 (Kitaguchi et al., 1988). These A751 and A770 proteins are abundant in many tissues. These three types of proteins are known to be generated by alternative splicing from the same APP gene (Kitaguchi at al., 1988; Ponte et al., Nature, 331: 525 (1988); Tanz et al., Nature, 331: 528 (1988). They are thought to be involved in cerebral amyloid deposition, because each has the β/A4 protein portion located on the C-terminal 99 amino acid fragment of APP (the N-terminal 28 amino acid part of this fragment is exposed outside the cell membrane, whereas a domain of β/A4 protein at its C-terminal side, comprising of 11–14 amino acids, exists inside of the cell membrane).

Immunohistochemical studies in the brains of patients with AD by using various antibodies raised against peptides corresponding to the several sites of APP have revealed that neuritic plaques can be stained by these antibodies (Wong et al., Proc. Natl. Acad. Sci., U.S.A., 82: 8729 (1985); Allsop et al., Neurosci. Lett., 68: 252 (1986); Shoji et al., Brain Res., 512: 164, (1990); Shoji et al., Am. J. Pathol., 137: 1027 (1990); Shoji et al., Brain Res., 530: 113 (1990). Therefore, amyloid proteins composing neuritic plaques in the AD patients can be easily recognized by these antibodies. By using these antibodies, one can trace the localization of APP and its metabolized derivatives in a brain of a transgenic animal overexpressing a human APP gene.

As APP is widely expressed in many tissues and is also evolutionally con served (there is a 97% homology at the amino acid level between mouse and human), it is postulated to play an important role an cell-cell interaction and/or neuronal cell differentiation (Shivers at al., EMBO. J., 7: 1365 (1988). Its precise role, however, is still unclear. Recently, it drew an attention that β/A4 protein at lower concentrations serve s as a growth stimulating factor for hippocampal matured neuronal calls, but it is neurotoxic at higher concentrations (Yankner et al., 1989). Interestingly, it was shown that the portion corresponding to the N-terminal 25th to 35th amino acid of βA4 protein is essential for both growth stimulating and inhibitory activities, and is homologous to the tachyquinin-type peptides (Yankner et al., 1989). More interestingly, when the purified β/A4 protein was injected into a cerebral cortex and a hippocampus of rats, a neuronal cell loss was induced as well as production of abnormally phosphorylated tau protein, a major constituent of PHF (Kowall et al., Proc. Natl. Acad. Sci., U.S.A., 88: 7247 (1991). These data suggest a close relationship between accumulation of β/A4 protein and PHF production. As another aspects of the role of APP, it has been reported that the C-terminal region of APP can be phosphorylated by protein kinase C and $Ca^{2+}$/calmodulin-dependent protein kinase II (Gandy et al., Proc. Natl. Acad. Sci., U.S.A., 85: 6218 (1988), and that $G_o$ protein, a major GTP-binding protein present beneath the cell membrane, can interact with APP (Nishimoto et al., Nature, 362: 75 (1993). These data suggest that APP is involved in signal transduction.

The APP gene is located on the long arm of the 21st chromosome in human (Goldgaber et al., Science, 235: 877 (1987)). Recently, in FAD (AD frequently occurs in people earlier than 65 years old), a mutation (from Val to Ile) was found at the amino acid position of 642 in human APP (based on the data of Kang et al., 1987; hereinafter, DNA and amino acid sequences of APP are based on the data of Kang et al., 1987) (Goate et al., Nature, 349: 704 (1991); Naruse et al., Lancet, 337: 978 (1991); Yoshioka et al., BBRC, 178: 1141 (1991); Hardy at al., Lancet, 357: 1342 (1991). Furthermore, other mutations (Val to Phe and Val to Gly) at 642 in APP have been found (Murrell J. et al., Science, 254: 97 (1991). These data suggest that mutation at $Val^{642}$ of APP would play an important role on the pathogenesis of FAD. In the case of Dutch-type AD which is frequently associated with hereditary cerebral hemorrhage, a mutation ($Glu^{618}$ to $Gln^{618}$) was found within the β/A4 protein part (Levy et al., Science, 248: 1124 (1990). Furthermore, two mutations ($Lys^{595}$ to $Asn^{595}$ and $Met^{596}$ to $Leu^{596}$) at the N-terminus of β/A4 protein were recently found in AD patients from a certain Swedish family (Mullan at al., Nature, Genet, 1: 345 (1992). This type of AD is called Swedish-type AD.

As described above, the molecular biological analysis of APP has been developed, but any effective information is not available yet as to why amyloid is accumulated and deposited in the brain of patients with AD, and how a neuronal cell is degenerated as a result of accumulation of β/A4 protein.

The present most exciting problem is that what kind of metabolic pathway of APP is profoundly involved in cerebral amyloid deposition. This matter is now being investigated extensively. For example, a membrane-bound C-terminal fraction of APP, 9 KD, could be extracted from human embryonic kidney-derived cell line 293 which had been transfected with expression vector DNA for APP cDNA, and the amino acid sequence of the N-terminus of the 9-kDa peptide was determined. As a result, APP was cleaved at the 16th Lys from the N-terminus of β/A4 protein (Esch at al., Science, 248: 1122 (1990). However, for deposition of cerebral amyloid, it requires that APP should be cleaved at both N-terminus and C-terminus of β/A4 protein and then aggregated. Therefore, insoluble β/A4 protein is not produced by the metabolic pathway of APP provided by Esch et al. (1990). Now, involvement of various metabolic systems and their defects would be considered as key factors for amyloid formation, but no clear answers have yet been obtained.

At present, it is considered that there are two pathways for APP processing; namely, 1) so-called secretary pathway, in which APP is processed into the secreted derivatives with molecular weights more than 100 KD ending at the 15th amino acid of β/A4 protein, and 2) so-called endosomal/lysosomal pathway, in which various APP peptides that are different in size but including a full length β/A4 protein portion are generated (Golde at al., Science, 235: 728 (1992).

Consequently, it has not yet been resolved how these two possible APP metabolic pathways are influenced by the mutations in the APP gene found in FAD, Dutch-type and Swedish-type AD. Probably, these APP mutants may allow the APP processing pathway to be entered into the endosomal/lysosomal pathway, not into the secretary pathway. In this connection, a transgenic animal system, in which overexpression of APP mutants are forced to be driven, will provide an useful tool for elucidating the mechanism underlying APP processing.

Recently, several reports have appeared relating to transgenic mice in which amyloid deposition was observed in their brains by overexpression of the full length or one part of human APP cDNA (Kawabata et al., Nature, 345: 476 (1991); Quon et al., Nature, 352: 239 (1991); Wirak at al. Science, 253: 323 (1991). However, the report by Kawabata at al. (1991) was later found to be not reproducible, and the paper was recently withdrawn (Nature, 356: 265, (1992). Furthermore, the report by Wirak at al. (1991) was later found to be misleading because the phenotypic change to AD-like character in APP-overexpressing transgenic mice was not caused by transgene expression (Science, 28, February, 1992). In addition, several published patent applications have reported that mouse transgenic model for AD are established (WO93/14200, WO93/02189, WO92/13069, WO92/06187, WO91/19810, EP451700 and WO 89/06689).

However, in each of these applications gene construction was only mentioned and/or only mentioned with indirect proofs only that the production of APP (not β/A4 protein) was observed. Furthermore, neither a neuronal cell loss nor formation of a neuritic plaque was mentioned in any report. Consequently, specific and distinct animal models for AD produced by genetic engineering technology are considered not yet to be established.

An important need therefore persists for an animal model of AD that exhibits the physiological and biochemical characteristics of this disease as described in human patients. This need has now been satisfied with the transgenic animal model of AD described below.

SUMMARY OF THE INVENTION

It is an object of this invention to provide a transgenic non-human animal that exhibits a human AD-like phenotype, that is, which displays several characteristics similar to symptoms associated with AD, such that the transgenic animal provides a useful model system for elucidating details of the pathogenesis of AD and for developing pharmaceuticals to inhibit AD onset and possibly to inhibit neuronal call death which is closely associated with AD.

This object has been realized by producing a transgenic non-human animal into which the APP gene is integrated and which overexpresses APP and metabolic polypeptide products in its brain to cause deposition of cerebral amyloid, and which exhibits phenotypical symptoms similar to those of the human AD (such as, massive production of APP appearance of abnormally phosphorylated tau protein, increase in the number of glial cells, and nuronal cell death).

In one embodiment of this invention, a transgenic non-human animal is provided that has integrated into its genome a recombinant DNA and a DNA-sequence necessary for allowing the C-terminal region of normal or mutant APP (including the β/A4 protein portion) to be expressed strongly in neuronal and other cells. The usefulness of the present invention resides, inter alia, in the facts that the inventive transgenic animal can be used to elucidate the mechanism of the disease (as is required for the design of drugs useful against the disease) and can be used for in vivo screening of anti-AD reagents.

These and other embodiments will become apparent from the specification and examples that follow and from the appended claims,

DETAILED DESCRIPTION OF THE INVENTION

Figure 1:
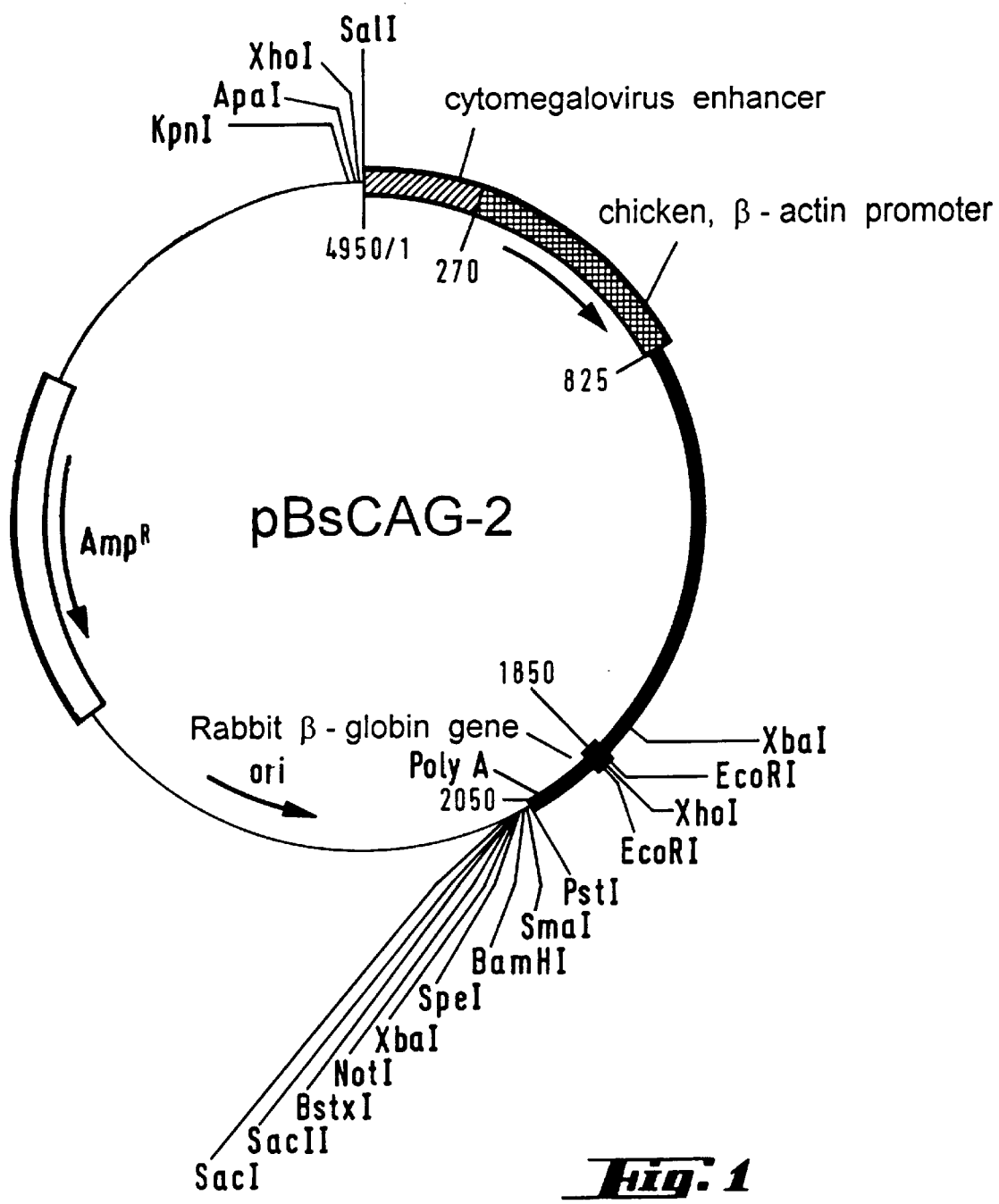
FIG. 1 shows a map for plasmid pBsCAG-2 having cytomegalovirus enhancer/ chicken β-actin promoter.

The present invention provides a tool for analyzing the molecular mechanism of APP synthesis and the pathogenesis of AD. More specifically, it provides the mechanism underlying APP processing after synthesis of this protein. More importantly, it provides an in vivo screening system for drugs that can inhibit synthesis and deposition of β/A4 protein, and thereby prevent or alleviate the symptoms of AD.

A DNA fragment encoding APP may be integrated into the genome of the transgenic animal by any standard method such as are described in Hogan et al., MANIPULATING THE MOUSE EMBRYO, Cold Spring Harbor Laboratory Press, 1986; Kraemer et al., GENETIC MANIPULATION OF THE EARLY MAMMALIAN EMBRYO, Cold Spring Harbor Laboratory Press, 1985; Krimpenfort et al., U.S. Pat. No. 5,175,384; Krimpenfort at al., Biotechnology, 9: 88 (1991), all of which are incorporated by reference. Preferably, the DNA fragment is microinjected into pronuclei of single-cell embryos in non-human mammalian animals, such as rodents such as mice, rabbits, cats, dogs or larger domestic or farm animals. These injected embryos are transplanted to the oviducts/uteri of pseudopregnant females and finally transgenic animals can be obtained. These transgenic animals are thought to overexpress the AD-related APP. The injected DNA contains an ubiquitous promoter to drive expression of the target protein in various types of the cells in transgenic mice. As β/A4 protein is generated from the C-terminal region of APP, overexpression of the C-terminus fragment of APP is considered to stimulate the formation of β/A4 protein leading to a neuronal call loss and a neuritic plaque formation, similar to AD.

The important point of the present invention is that overexpression of the C-terminal region of APP which includes the β/A4 protein portion is possible in neuronal calls and other types of cells under the control of a strong and ubiquitous promoter. Then, as a result, the following phenotypic alteration can be elicited: AD-specific amyloid deposition at hippocampus, appearance of abnormally phosphorylated tau protein, increase in the number of glial cells, alteration in the alternative splicing pattern of endogenous mouse APP transcripts, neuronal cell death near hippocampus and reduced behavioral activity. Another important point of the present invention is that transgenic mice shaving the DNA sequence encoding APP mutants, in which at least one amino acid replacement occurs in β/A4 protein, could be successfully created. With this invention, the massive accumulation of a cerebral amyloid would occur, because the mutant APPs tend to be frequently transferred to the endosomal/lysosomal pathway of APP and/or possibly become insensitive against proteolytic cleavage leading to formation of β/A4 protein. Accordingly, the transgenic animal disclosed in the present invention provides a useful system to analyze the interaction between APP and APP-processing protease in vivo, and the interaction between the endogenous mouse APP and the introduced human APP. They will also be useful for screening anti-AD drugs in vivo.

An important characteristic of the present invention is that the transgenic animals produced thereby are defined as "true" animal models for AD, compared with any previously known APP-expressing transgenic animals, because the present transgenic animals exhibit a series of symptoms phenotypic for human AD, including, massive production of APP, appearance of abnormally phosphorylated tau protein, increase in the number of glial cells, neuronal cell death, etc.).

One embodiment of the present invention comprises a transgenic non-human mammalian animal containing a DNA encoding the C-terminal region of human APP containing about the first 99 to 103 amino acids of APP, in particular the amino acid sequence of I.D. NO: 4 or 10, said DNA being integrated into the somatic and germ cells of the animal. In another embodiment, the transgenic animal contains mutant human APP containing the amino acid sequence I.D. NO: 6 wherein glutamic acid at position 22 of SEQ I.D. NO: 4 is converted to glutamine, the amino acid sequence I.D. NO: 8 wherein value at position 46 of SEQ I.D. NO: 4 is converted to isoleucine; the amino acid sequence I.D. NO: 12 wherein lysine at position 3 of SEQ I.D. NO: 10 is converted to asparagine; and, methionine at position 4 of SEQ I.D. NO: 10 is converted to leucine.

A preferred embodiment of the present invention is a transgenic animal containing a DNA integrated into the somatic and germ cells wherein the DNA encodes a signal peptide. In a particularly preferred embodiment, the DNA encodes a signal peptide of human β-amyloid precursor protein, more particular a signal peptide with the amino acid sequence of I.D. NO: 2 and the above-mentioned C-terminal regions of human APP.

Another embodiment of the present invention is a transgenic animal wherein said integrated DNA is controlled by an ubiquitous promotor, in particular the β-actine promotor, and an enhancer, in particular the cytomegalovirus enhancer.

Yet another embodiment of the invention relates to a method of producing a transgenic animal of the present invention wherein the exogenous DNA is microinjected into the nucleus of single-cell stage embryos or wherein the exogenous DNA is introduced into preimplantation embryos with the aid of retroviral vector DINA.

The transgenic animal can be used as an Alzheimer's disease model as already explained above because the animal of the present invention shows the following histopathological characteristics in the hippocampus;

1) synthesis in large quantity of C-terminus peptide of β-amyloid precursor protein, 2) death of neuronal cell in pyramidal cells at CA regions, 3) increase of glial cells, and 4) deposition of abnormally phosphorylated tau protein.

Therefore, another embodiment refers also to the use of the transgenic animals of the present invention for the screening of drugs against Alzheimer's disease.

The following examples, which are provided merely to exemplify the invention, should not be construed as limiting the invention in any way, said invention being described in the entire specification and appended claims.

EXAMPLES

In this invention, the following examples are intended to disclose and describe completely how to make DNA sequences, fusion gone constructs, transgenic mice, etc. However, it should not be construed that the invention is limited to these specific examples.

EXAMPLE 1

Construction of plasmids pβA/NORβ, pβA/FADβ, pβA/Dβ, pβA/ΔNORβ and pβA/NLβ

The target gene to be expressed in the animal was constructed as follows. The sequence encoding a signal peptide (at amino acid positions of 1–17) of normal human APP and the sequence encoding the C-terminal portion including the β/A4 protein portion; (at amino acid positions of 597–695). This fusion gene (hereafter called NORβ) was synthesized according to the method of Horton et al. (Gene, 77: 61 (1989). First, a human brain cDNA library was synthesized by the RT (reverse transcription)-PCR method from an embryonic human brain poly(A) RNA (#6516-1; Clontech). The primers used were reverse primer BAPP-6 (SEQ ID No.: 13), sense primer BAPP-7 (SEQ ID No.: 14), sense primer BAPP-10 (SEC ID No.: 15) and reverse primer BAPP-12 (SEQ ID No.: 16). By using these primers, NORβ was successfully synthesized. The resulting NORβ was next fractionated through electrophoresis in a 2% agarose gel. The isolated NORβ was digested with Xbal and inserted into the Xbal site of a cloning vector pGEM3Z(-) (Promega) to create pGEM3Z/NORβ. This recombinant plasmid was then amplified in *E. coli* and purified. The purified plasmid DNA was sequenced by a dideoxy chain-termination method (Sanger et al., Proc. Natl. Sci., U.S.A., 74: 5463 (1977), and was confirmed that the inserted NORβ sequence had the correct sequence as previously reported (Kang at al., 1987).

Dβ (a DNA sequence formed by combining SEQ ID No.: 1 with SEQ ID No.: 5) and FADβ (a DNA sequence formed by combining SEQ ID No.: 1 with SEQ ID No.: 7) are basically the same as NORβ, except that 1) Dβ has a mutation (Glu$^{618}$ to Gin$^{618}$) in APP which is found in Dutch families with a hereditary amyloid angiopathy and FADβ a mutation (Val$^{642}$ to Ile$^{642}$) in APP which is found in families with FAD, and 2) both Dβ and FADβ have additional about 30 bp 3' non-translated region of human APP cDNA (Kang at al., 1987) at their 3' side. These were synthesized by PCR method of Horton at al. (1989) from the human cDNA library as mentioned previously. In case of synthesis of Dβ, reverse primer BAPP-8 (SEQ ID No.: 17), sense primer BAPP-2 (SEQ ID No.: 18) and reverse primer BAPP-15 (SEQ ID No.: 19) as well as BAPP-10, BAPP-6 and BAPP-7 were used. In case of FABβ, reverse primer BAPP-3 (SEQ ID No.: 20), sense primer BAPP-9 (SEQ ID No.: 21) and BAPP-15 as well as BAPP-10, BAPP-6 and BAPP-7 were used.

ΔNORβ (a DNA sequence for Met is added to the N-terminal portion for the sequence of SEQ ID No.:10, peptide) is basically the same as NORβ, except that a sequence for the signal peptide consisting of 17 amino acids is missing. ΔNORβ was synthesized by PCR using PGEM32/NORβ as a template DNA. The primers used were sense primer BAPP-13 (SEQ ID No.: 22) and BAPP-12. The amplified fragment was then cloned into PGEM3Z(-). The insert was sequenced to confirm that the sequence of the insert was correct.

NLβ (a DNA sequence for Met was added to the N-terminal portion of the sequence encoding a peptide described in SEQ ID No.: 12) was PCR-amplified as with the synthesis of ΔNORβ, using sense primer BAPP-14 (SEQ ID No.: 23) and BAPP-12. The amplified fragment was cloned into PGEM3Z (–). The insert was sequenced to confirm that the sequence of the insert was correct. NLβ, a mutant APP gene found in Swedish-type AD, has two mutations (Lys$^{595}$to Asn$^{595}$ and Met$^{596}$ to Leu$^{596}$) in the N-terminal region of A/A4 protein.

Figure 2:
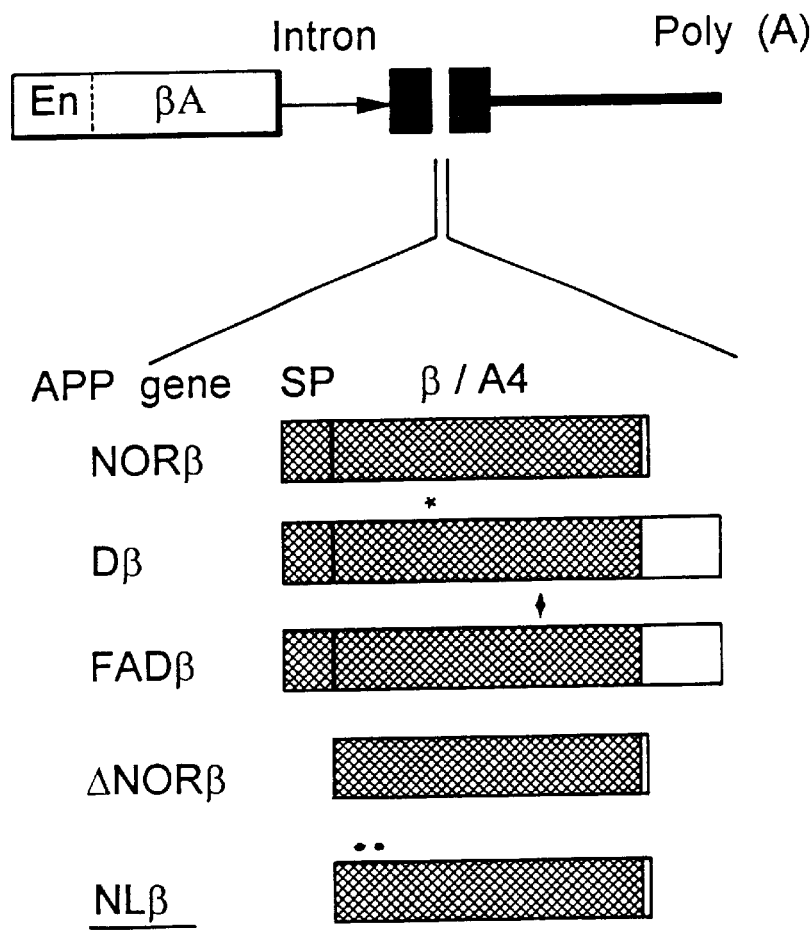
FIG. 2 shows transgenes in which cytomegalovirus enhancer/chicken β-actin promoter element is combined with NORβ, Dβ, FADβ, ΔNORβ and NLβ.

Expression vectors to express the genes described above were constructed as follows. A 2.3-kb fragment containing cytomegalovirus enhancer/chicken β-actin promoter element was isolated by digestion with SalI/PstI of a mammalian expression vector pCAGGS (Niwa at al., Gene, 108: 193 (1991) and inserted into the SalI/PstI sites of a cloning vector pBluescript (Stratagene) to create pBsCAG-2 (FIG. 1). In the 2.3-kb fragment containing the above described enhancer/promoter, a part of rabbit β-globin gene (composed of the 2nd intron, the 3rd axon and 3' non-translated region) is also included. Generally, a target gene (i.e. cDNA) to be expressed can be inserted into the EcoRI site of the 3rd exon of rabbit β-globin gene in pBsCAG-2. The above described NORβ, FADβ, Dβ, ΔNORβ and NLβ genes were inserted into pBsCAG-2 to create pfβ/NORβ, pβA/FADβ, pβA/Dβ, pβA/ΔNORβ and pβA/NLβ which will be used for expression of the target genes in transgenic mice (FIG. 2). For DNA introduction into mouse single-cell stage embryos, the transgene was isolated from each fusion construct by digestion with SalI/BamHI and used. DNA digestion, ligation and isolation. Also, DNA sequence at the junctional region between the insert and the vector was confirmed by sequencing.

EXAMPLE 2

Recovery of Single-Cell Stage Embryo and DNA Introduction into It

One-cell stage embryos were recovered from the oviducts off B6C3F1 female mice that had been already mated with male mice. The recovered embryos are still in an early stage of pronucleate stage. Therefore, both ale and female pronuclei can be easily distinguishable because they are separated from each other. Cumulus calls surrounding oocytes were removed by hyaluronidase treatment, washed properly and incubated at 37° C. in an atmosphere of 5% $CO_2$ in air, for a certain time prior to DNA injection. Preferably, it is kept in a drop (50 μl) of M-16 egg culture medium (Whittingham, J. Reprod. Fert., 4: 7 (1971) covered with paraffin oil on a bacteriological dish with 30 mm diameter (No. 333656, Nunc). The fusion construct containing a transgene was prepared by the above-mentioned method. Any of the above-mentioned fusion constituents can be cloned, and can be introduced into the pronuclei of 1-cell stage embryos according to the method mentioned herein.

Next, the explanation shall be given in detail on the introduction of DNA obtained from a NORβ-expression vector (pβA/NORβ). This method can also be applied for other fusion constructs than pΔA/NORβ.

First, pΔA/NORΔ was extracted after cloning into the host *E. coli* and subsequent cultivation. For further purification, the extracts were ultra-centrifugated in cesium chloride and dialyzed after removal of ethidium bromide. Transgene can be isolated after digestion of these purified plasmid DNAs with certain restriction enzymes (in this case SalI and BamHI were used) and subsequent electrophoresis in a 0.8% agarose gel. The obtained transgene was micro-injected into single-cell stage embryos by using an injection pippet with a 1 μm outside diameter ( Hogan et al., Manipulating the Mouse Embryo, 1986). About 10 μm of DNA solution containing transgenes (about 1 ,000 copies of transgenes per pl) were sucked and the DNA was injected into the males pronucleus. The injected embryos were incubated for several hours to one day and then transplanted to the oviducts of pseudopregnant ICR foster mothers of Day 1 of pregnancy (the day when a vaginal plug is recognized is defined as Day 1 of pregnancy). The transplanted foster mothers were fed until a delivery of fetus. After delivered, neonates were nursed by the foster mothers for one month until weaning. Then, they were served for Southern blot analysis of a tail DNA. The $F_o$ (founder) mouse, judged as transgenic, was mated with other non-transgenic mouse to obtain F1 transgenic offspring. These $F_1$ transgenic offspring can be cryopreserved in a form of eggs or spermatozoa. After this, all the $F_1$ transgenic offspring and their non-transgenic litermates were killed on 110 to 30 weeks after birth for Northern blot hybridization and pathological analyses.

As one of the examples, the results obtained from the injection of fβ-NORβ transgene into mouse single-cell stage embryos are shown in Table 1. Illustrated therein are the number of neonates per the number of surviving fetuses after DNA injection and transfer to recipients and the number of $F_o$ mice judged as transgenic.

TABLE 1

Productive Efficiency of Transgenic Mice having βA-NORβ transgene

| Transgene | Number of neonates/Number of transplanted embryos (%) | Number of Transgenic mice (%) |
| --- | --- | --- |
| βA-NORβ | 120/560 (21) | 35 (29) |

As shown in Table 1, 35 of 120 mice born were transgenic. When these transgenic mice were continuously observed, one line (0304) became inactive around 10 weeks after birth and another one line (1102) showed hydrocephaly. The other transgenic animals looked normal until about 110 to 30 weeks after birth. Gametes were collected and deep-frozen before sampling for molecular and pathological analyses. After this, brains from these transgenic samples were screened by Northern and Western blot analyses to identify NORβ-higher expressing lines and 5 lines showing strong expression of NORβ (0202, 0304, 1002, 1102 and 1301) were finally selected. The following is provided mainly from the analysis of these 5 lines.

EXAMPLE 3

Transgene-Derived mRNA Expression

Transgene-derived mRNA expression was analyzed by Northern blot hybridization for βA-NORβ transgenic lines (including 0304 and 11002). Total cellular RNA was isolated from organs (including brains) of transgenic and non-transgenic mice. The isolated RNA (20 μg) was electrophoresed in 1.1% agarose/1.1M formaldehyde gel and then blotted onto a nylon membrane filter. Prehybridization was carried out for 2 hours at 42° C. in a hybridization buffer [5×SSC (1×SSC=0.15M NaCl, 15mM Na-citrate, pH 7.4), 50% formamide, 5mM EDTA, 5mg/ml heat-denatured salmon DNA and 5×Denhardt's solution]. The DNA probe (containing a NORβ fragment) was heat-denatured after labelling with $^{32}$P by random prime labelling method and added to the hybridization buffer. Hybridization was performed for 18 hours at 42° C. The filters were washed for 20 minutes at 56° C. in a solution containing 0.1×SSCand 0.1%

Figure 3:
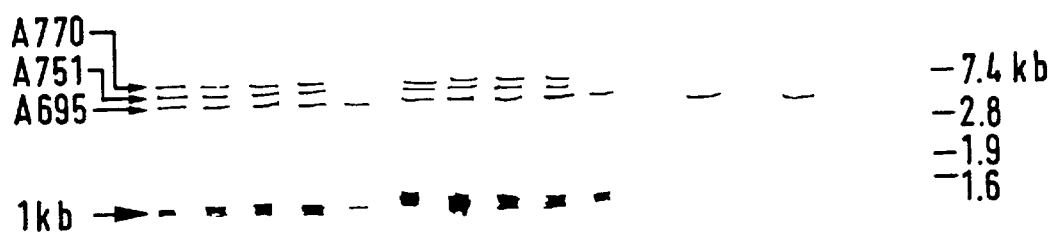
FIG. 3 shows a result from Northern blot analysis of various tissues from βA-NORβ transgenic mice (1102 and 0304) and a non-transgenic mouse. The size of molecular weight is shown as kb and the molecular weight markers are described in the right side of the drawing.

SDS. The filters were exposed to Kodak xAR-5 film with a intensifying screen for 24 to 72 hours at -80° C. An example of the Northern blot analysis is shown in FIG. 3. RNAs loaded were from NORβ-higher expressing lines (0304 and 1102) and a non-transgenic mouse. The organs investigated were brain, liver, kidney, intestine and testis. On the brain of 0304 line, there observed about 10 times higher expression of transgene-derived mRNA (about 1 kb in size) than that of endogenous mouse A695 mRNA (about 3.4kb in size). The level of NORβ mRNA in the 1102 sample was slightly lower than that in the 0304 sample. However, non-transgenic sample had no transgene-derived mRNA. A similar tendency was observed in other organs. Interestingly, there was an increase in the amount of A695 mRNA in the transgenic mice (for example, see the liver samples of 1102 and 0304). Similar increase in the level of A751 (about 3.8 kb in size) and A770 (about 3.85 kb in size) mRNAs was observed (for example, see the brain samples of 1102 and 0304). it is considered that this may reflect the altered alternative splicing pattern of endogenous mouse APP mRNA, possibly due to overexpression of the exogenous NORβ.

EXAMPLE 4

Western Blot Analysis

The expression pattern of APP in the brains from βA-NORβ transgenic mice and non-transgenic mouse (control) was determined by Western blot analysis. Protein homogenate was prepared from a whole or 3/4 brain according to the method of Shivers et al. (1988). A sample (50 μg) was electrophoresed in 10/16% Tris-tricine SDS gel and transferred to immobilm-P membranes by electroblotting. The blot was reacted with the anti-APP antibody, W61C, diluted at 1/500 (rabbit antibodies raised against the C-terminal peptide between amino acid positions of 660 and 695 in APP; Shoji M. et al., 1990c) in order to detect APP using non-RI ECL detection system (Amersham).

Figure 4:
FIG. 4 shows a result from Western blot analysis of cerebral extracts from βa-NORβ transgenic mice and a non-transgenic mouse. The antibody used is anti-APP antibody, W61C.

An example of Western blot analysis is shown in FIG. 4. In FIG. 4, the results of a total of 11 transgenic mice and a non-transgenic mouse are shown. Namely, some bands near about 120-kDa, corresponding to the previously reported mammalian animal APP isoforms, were detected in the brain and other organs from the non-transgenic control mouse and transgenic mice. Furthermore, a remarkable increase in the level of NORβ-derived protein (11.4 Kd) was observed. Especially, a high expression (5 to 6 times) was observed in the transgenic samples from 0202, 1002 and 1301 liness. However, none of bands at 4.2 kD which correspond to β/A4 protein were detectable by this procedure. It is considered that β/A4 protein is not produced in the transgenic brains examined or may be scarce if produced.

EXAMPLE 5

Immunohistochemical Analysis of Mouse Brains using Antibodies

In order to analyze the transgene expression in detail at tissue or cellular level, immunohistochemical staining was performed for organs (including brain) from transgenic and non-transgenic mice by using anti-APP antibodies. The mice investigated were 3 lines having βA-NORβ and non-transgenic mice.

Mice were anaesthetized with pentobarbital and organs were excised. These organs were then fixed in 4% paraformaldehyde (in PBS) for 1–3 days, embedded in paraffin and sectioned at 5 μm thickness. The specimens were dewaxed, dehydrated, treated with 0.5% periodic acid for 0.5 hours, blocked with normal goat serum and reacted with the antibody diluted to 1/500. The reaction was carried out for 3 hours at room temperature, reacted with biotinylated anti-rabbit IgG for 2 hours at room temperature, and then reacted with ABC (avidin-biotin peroxidase complex). These reactions were carried out according to the procedure recommended by the manufacturer (ABC Kit; Vector Co., Burlingame, U.S.A.). Peroxidase activity can be visualized by incubation with a substrate, 3,3'-diamino-benzidine (DAB)/NiCl$_2$. Counterstaining was performed with methyl green. Some of the specimens were Nissul-stained in order to detect neuronal cells more clearly.

Figure 5A:
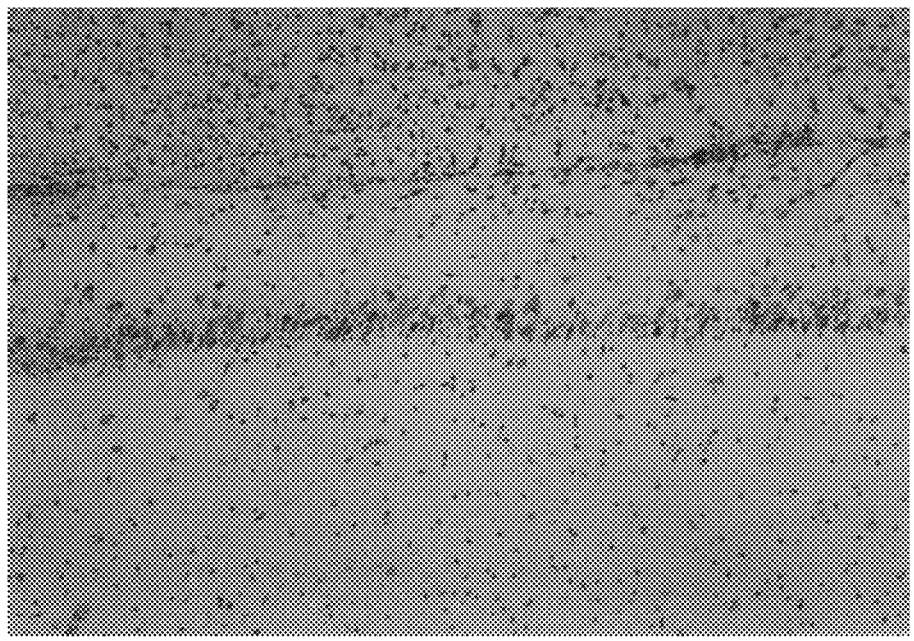
FIG. 5 (A–B) shows microphotographs showing Nissul-staining of hippocampus of βA-NORβ-304 transgenic mouse brain (A) and a non-transgenic mouse brain (B).
Figure 5B:
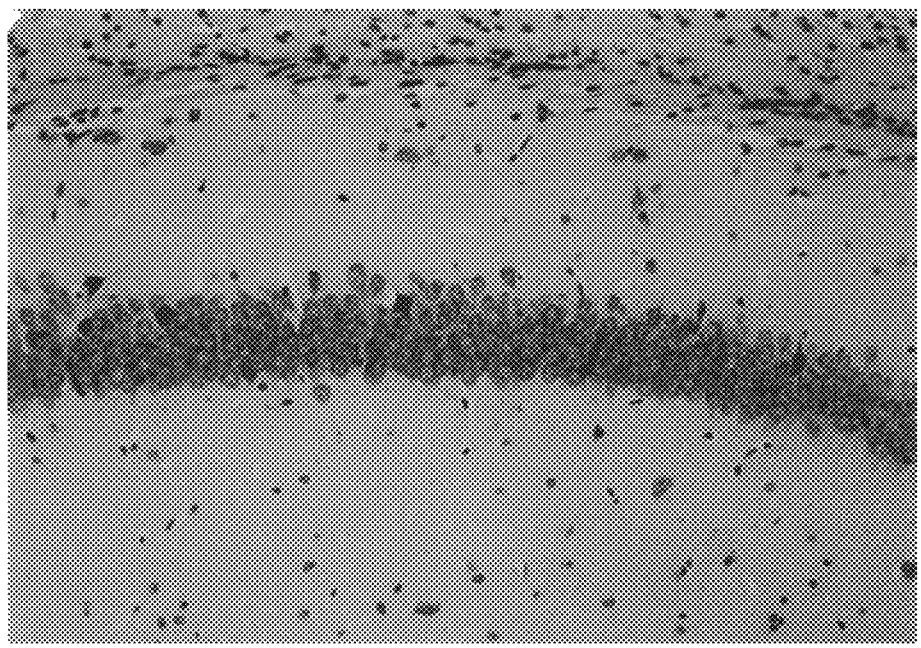

Nissul-staining of the brains from transgenic mice of βA-NORβ-0304 line and a non-transgene mouse revealed that a neuronal cell loss was found in the transgenic samples; especially remarkable is the pyramidal layer of CA3 region of hippocampus as shown in FIG. 5.

Figure 6A:
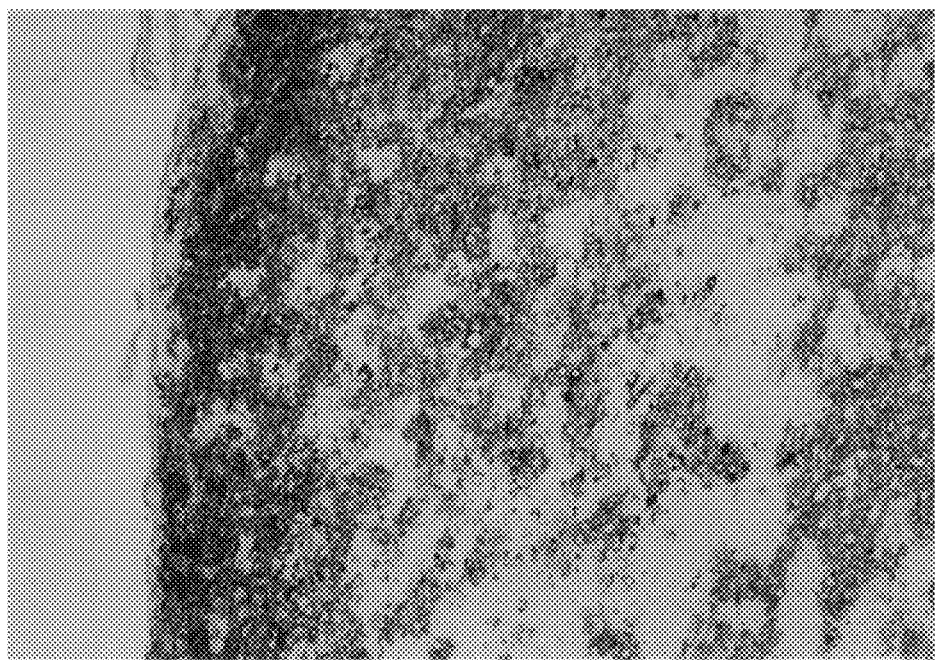
FIG. 6 (A–B) shows microphotographs showing immuno reaction of a cortex region with βA-NORβ-0304 transgenic animal brain (A), and a non-transgenic mouse brain (B), by using anti-APP antibody, W61C.
Figure 6B:
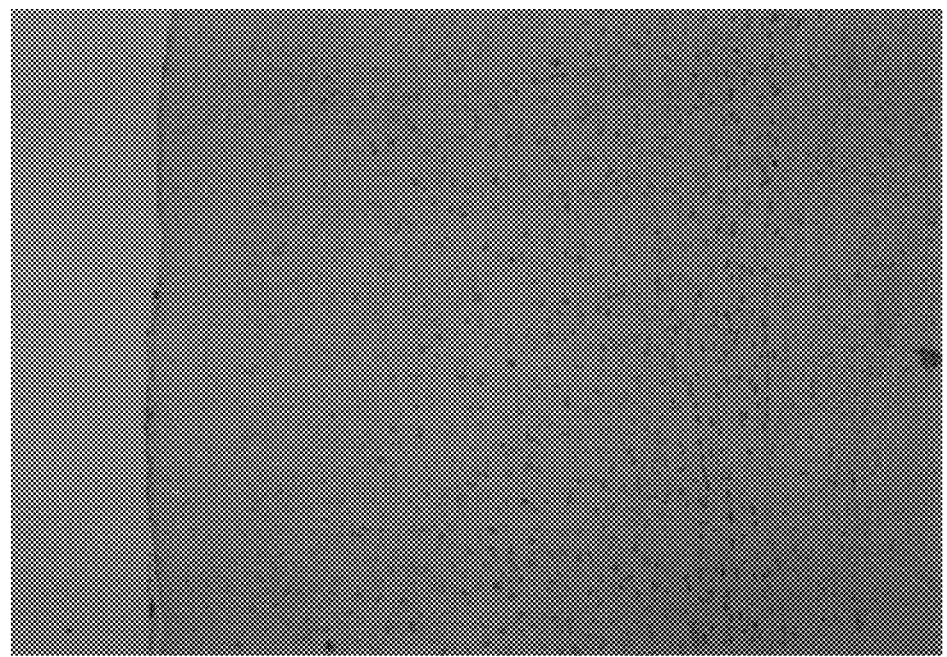

Immunohistochemical staining of the brains from βA-NORβ-0304 transgenic and its non-transgenic littermate by W61C, one of the anti-APP antibodies revealed that a strong immuno-reaction was observed in neuronal cells of a cerebral cortex and a hippocampus of transgenic mice, compared with those from the non-transgenic mice as shown in FIG. 6. In addition, positive reaction was also observed in many neuronal processes. Similar observation was made by using other antibodies, W63N, raised against the N-terminal region of APP peptide (18th to 38th) (Shoji M. at al, 1990c). However, mesencephalon, brain stem and cerebellum were unreactive with these antibodies.

Figure 7A:
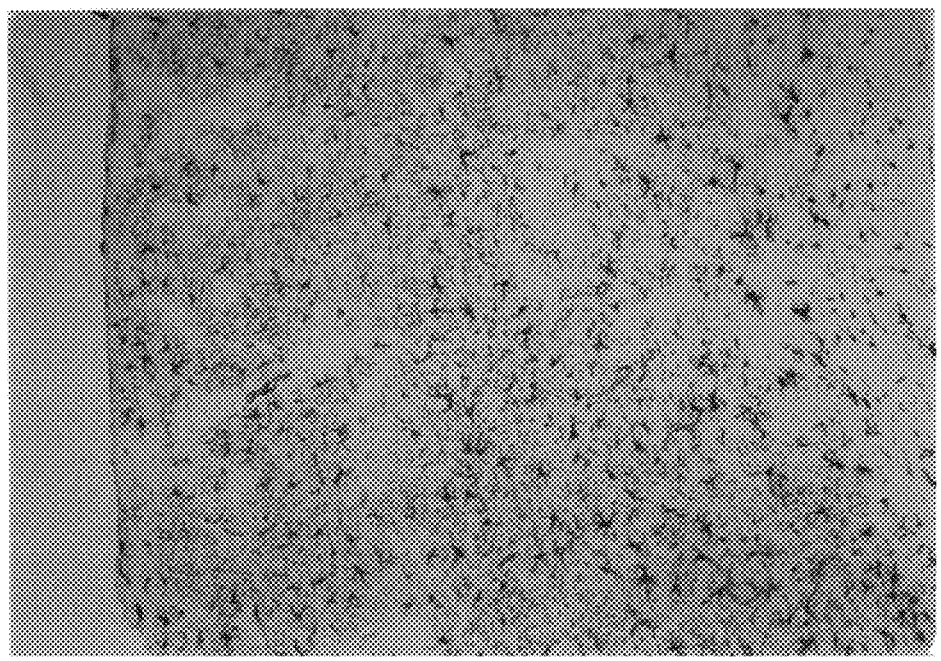
FIG. 7 (A–B) shows microphotographs of immuno reactive products produced by anti-GFAP antibody in βA-NORβ-0304 transgenic animal brain (A) and a non-transgenic mouse brain (B).
Figure 7B:
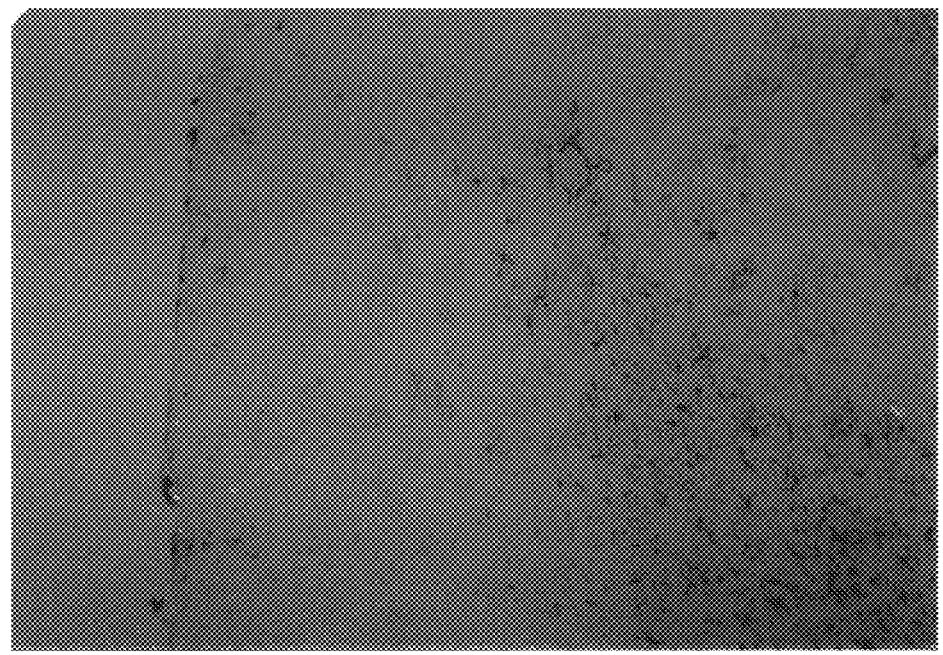

A remarkable increase in the number of glial cells was observed in the cortex, hippocampus and forebrain basement of the transgenic mice when evaluated by anti-GFAP (glial fibrillary acidic protein) antibody which specifically recognizes glial cells as shown in FIG. 7. This increase in the number of glial cells is considered to be closely associated with AD (Beach at al., Glia, 2: 420 (1989). As perhaps predicted from FIG. 5, glial cells may proliferate in order to compensate the space generated along with a neuronal cell loss.

Figure 8A:
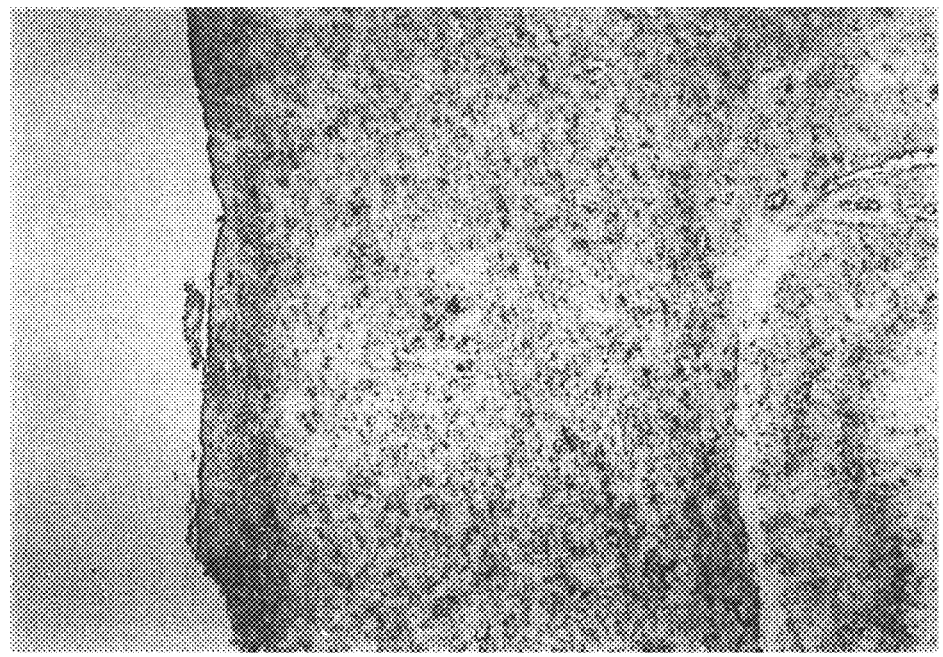
FIG. 8 (A–B) shows microphotographs of immunoreactive products produced by anti-tau antibody, β1-28, in βA-NORβ-0304 transgenic animal brain (A) and a non-transgenic mouse brain (B).
Figure 8B:
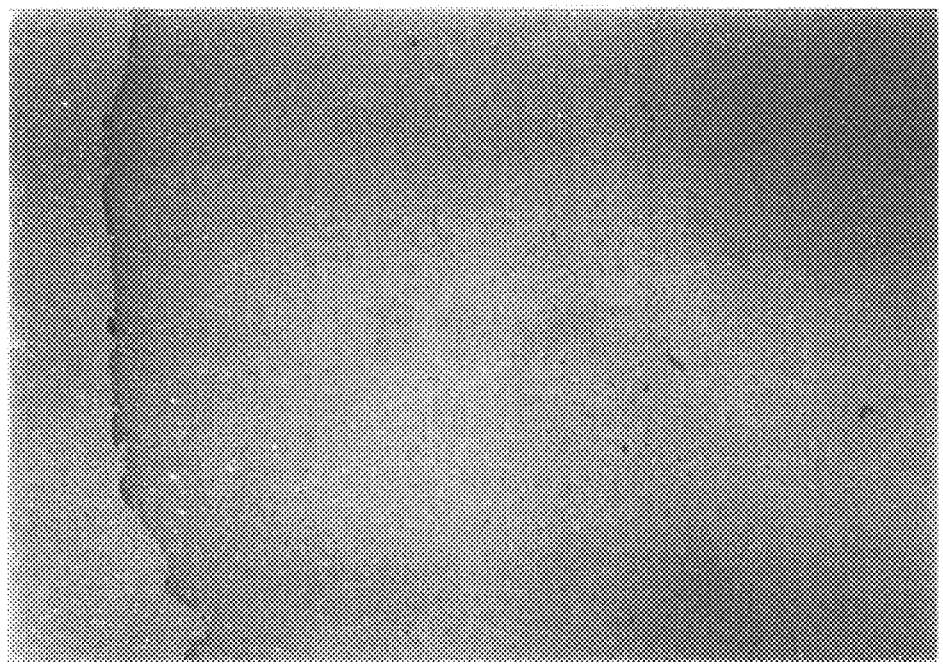

When brain specimens from βA-NORβ-0304 transgenic and non-transgenic mice were reacted with the antibody β1-28 (Iharara. et al, Nature, 304: 727 (1983) which specifically recognizes the abnormally phosphorylated tau protein, cells within and around the hippocampal region of the transgenic mice were stained as shown in FIG. 8(A). No positive reaction was observed in the non-transgenic brains as shown in FIG. 8(B).

Figure 9A:
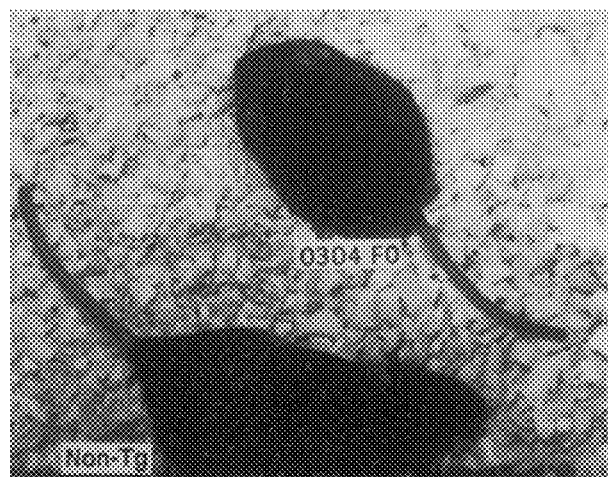
FIG. 9 (A–B) shows pictures of βA-NORβ-0304 transgenic mouse (center in the figure) and a non-transgenic mouse (upper in the figure) (A) and of βA-NORβ-0304 transgenic mouse (B).
Figure 9B:
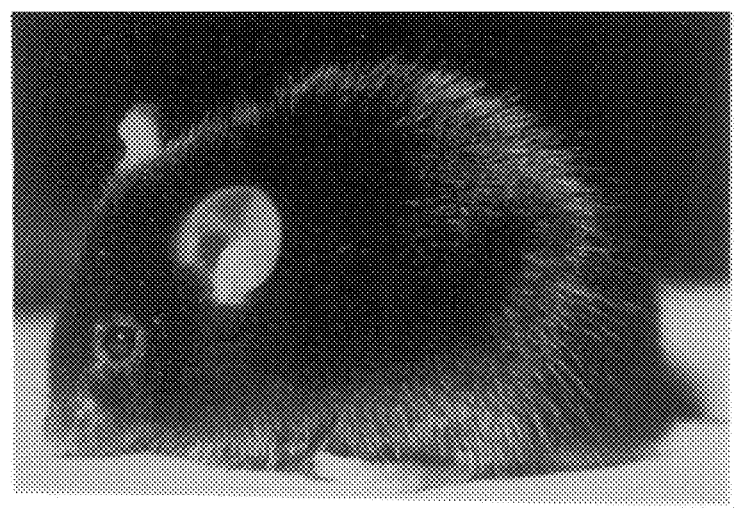

Whole pictures of βA-NORβ-0304 transgenic mouse and its non-transgenic littermate are shown in FIG. 9. FIG. 9(A) shows βA-NORβ-0304 transgenic mouse (center in the figure) and non-transgenic mouse (upper in the figure) and FIG. 9(B) shows βA-NORβ-0304 transgenic mouse alone.

The transgenic mice described in this invention can be utilized for screening drugs that are able to decrease parameters (i.e., anti-β/A4 protein antibody-reactive substance, anti-abnormally phosphorylated tau protein antibody-reactive substance, etc.) associated with AD. For example, the drug to be assayed can be administrated simultaneously to both the transgenic and non-transgenic control animals. This drug may be administrated continuously for a period sufficient to influence the above-described parameters in animal brains or to inhibit neuronal cell death. After administration of the drug, test animals, e.g., mice, may be analyzed histologically for brain abnormalities and molecular biologically. By comparing the above described parameters between transgenic and control animals, a decision whether the drug used is effective or not can be made.

We claim:

1. A transgenic mouse whose somatic and germ cells comprise a transgene operatively linked to a β-actin ("βa") promoter, wherein said transgene encodes a 99 to 103 amino acid carboxy-terminus of human β-amyloid protein, wherein said transgene is further operatively linked to an enhancer, wherein expression of said transgene results in said mouse exhibiting β-amyloid deposits in its brain; neuronal cell death; abnormally-phosphorylated tau protein; an increase in the number of glial cells; an alteration in the splicing pattern of endogenous APP transcripts; and reduced behavioral activity in tests selected from the group consisting of open field test, a passive avoidance test, and a Morris-type water maze test.

2. The transgenic mouse according to claim 1, wherein the transgene further is operatively linked to a DNA sequence encoding a signal peptide.

3. The transgenic mouse according to claim 2, wherein said signal peptide is SEQ ID NO: 2.

4. The transgenic mouse according to claim 1, wherein said enhancer is the cytomegalovirus enhancer.

5. The transgenic mouse according to claim 1, wherein said transgene is βa-NORβ.

6. The transgenic mouse according to claim 1, wherein said transgene is βa-ΔNORβ.

7. The transgenic mouse according to claim 1, wherein said transgene is βa-Dβ.

8. The transgenic mouse according to claim 1, wherein said transgene is βa-FADβ.

9. The transgenic mouse according to claim 1, wherein said transgene is βa-NLβ.

10. The transgenic mouse according to claim 1, wherein the transgene is selected from the group consisting of SEQ ID NOS: 4, 6, 8, 10 and 12.

11. A method of producing a transgenic mouse according to claim 1, comprising microinjecting into a mouse embryo a transgene operatively linked to a β-actin promoter, wherein said transgene encodes a 99 to 103 amino acid carboxy-terminus of human β-amyloid protein, wherein said transgene is further operatively linked to an enhancer, wherein expression of said transgene results in said mouse exhibiting β-amyloid deposits in its brain; neuronal cell death; abnormally-phosphorylated tau protein; an increase in the number of glial cells; an alteration in the splicing pattern of endogenous APP transcripts; and reduced behavioral activity in tests selected from the group consisting of open field test, a passive avoidance test, and a Morris-type water maze test.

12. The method according to claim 11, wherein the transgene further is operatively linked to a DNA sequence encoding a signal peptide.

13. The method according to claim 12, wherein said signal peptide is SEQ ID NO:2.

14. The method according to claim 11, wherein said enhancer is the cytomegalovirus enhancer.

15. The method according to claim 11, wherein the transgene is selected from the group consisting of SEQ ID NOS: 4, 6, 8, 10 and 12.

16. A method of screening a drug for activity against Alzheimer's Disease, comprising administering said drug to transgenic mouse whose somatic and germ cells comprise a transgenic operatively linked to a β-actin ("βa") promoter, wherein said transgene encodes a 99 to 103 amino acid carboxy-terminus of human β-amyloid protein, wherein said transgene is further operatively linked to an enhancer, wherein expression of said transgene results in said mouse exhibiting β-amyloid deposits in its brain; neuronal cell death; abnormally-phosphorylated tau protein; an increase in the number of glial cells; an alteration in the splicing pattern of endogenous APP transcripts; and reduced behavioral activity in tests selected from the group consisting of open field test, a passive avoidance test, and a Morris-type water maze test, and monitoring said mouse for the effects of said drug on β-amyloid deposits in its brain; neuronal cell death; abnormally-phosphorylated tau protein; an increase in the number of glial cells; an alteration in the splicing pattern of endogenous APP transcripts; and reduced behavioral activity in tests selected from the group consisting of open field test, a passive avoidance test, and a Morris-type water maze test.

17. The method according to claim 16, wherein the transgene further is operatively linked to a DNA sequence encoding a signal peptide.

18. The method according to claim 17, wherein said signal peptide is SEQ ID NO:2.

19. The method according to claim 16, wherein said enhancer is the cytomegalovirus enhancer.

20. The method according to claim 16, wherein said transgene is selected from the group consisting of signal peptide is SEQ ID NOS: 4, 6, 8, 10 and 12.

* * * * *